(12) United States Patent
Jackson et al.

(10) Patent No.: US 8,541,626 B2
(45) Date of Patent: Sep. 24, 2013

(54) METHOD FOR SYNTHESIS OF KETONES FROM PLANT OILS

(75) Inventors: Michael A. Jackson, Morton, IL (US); Steven C. Cermak, Galesburg, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/356,731

(22) Filed: Jan. 24, 2012

(65) Prior Publication Data
US 2013/0190535 A1 Jul. 25, 2013

(51) Int. Cl.
*C07C 45/00* (2006.01)
*B01J 23/10* (2006.01)
*B01J 23/08* (2006.01)
*B01J 23/56* (2006.01)

(52) U.S. Cl.
USPC ............ 568/391; 502/304; 502/332; 502/355

(58) Field of Classification Search
USPC ....................................... 568/397
See application file for complete search history.

(56) References Cited

U.S. PATENT DOCUMENTS 7,288,573 B2   10/2007   Roe

OTHER PUBLICATIONS

Tyurin et al. Phase equilibriums in the interaction of cerium and aluminum with oxygen and sulfur in molten iron. Izvestiya Akademii Nauk SSSR, Metally (1983), vol. 2, pp. 22-26; HCAPLUS abstract, Document Number: 98:183455.*

Duan, Jian-li, et al, "Preparation of 2-Undecanone by Gas-Solid Catalysis", Wuhan University Journal (Natural Science Edition), Feb. 2005.
Gaertner, Christian A., et al., "Ketonization of Carboxylic Acids and Esters over Ceria-Zirconia as Biomass-Upgrading Processes", Ind. Eng. Chem. Res., 2010, vol. 49, No. 13, pp. 6027-6033.
Glinski, M., et al, "Catalytic ketonization over oxide catalysts X. Tranformations of various alkyl heptanoates", Applied Catalysis A: General 281, 2005, pp. 107-113.
Hendren, Travis S., et al., "Kinetics of catalyzed acid/acid and acid/aldehyde condensation reactions to non-symmetric ketones", Catalysis Today, 85, 2003, pp. 333-351.
Leung, Anna, et al., "Pathway for the Catalytic Conversation of Carboxylic Acids to Hydrocarbons over Activated Alumina", Energy & Fuels, 1995, 9, pp. 913-920.
Randery, Sandeep D., et al., "Cerium oxide-based catalysts for production of ketones by acid condensation", Applied Catalysis A: General, 226, 2002, pp. 265-280.
Renz, Michael, et al., "Ketonization of Carboxylic Acids by Decarboxylation: Mechanism and Scope", Eur. J. Org. Chem., 2005, pp. 979-988.
Vonghia, Enrico, et al., "Pathways for the Deoxygenation of Triglycerides to Aliphatic Hydrocarbons over Activated Alumina", Energy & Fuels, 1995, 9, pp. 1090-1096.

\* cited by examiner

*Primary Examiner* — Sikarl Witherspoon
(74) *Attorney, Agent, or Firm* — John Fado; Randall E. Deck; Lesley Shaw

(57) ABSTRACT

Ketones may be produced in high yields from glycerides of short chain fatty acids by reaction with a carboxylic acid. The reaction is conducted in the presence of a catalyst and under conditions effective for ketonization of decanoate with the carboxylic acid to produce free ketones. Reaction of a glyceride comprising at least one ester of decanoic acid with a carboxylic acid selected from acetic acid and/or propionic acid produces 2-undecanone and/or 3-dodecanone, respectively. Catalysts of the formula $Fe_mCe_nAl_pO_x$, wherein m is between about 0.2 to about 0.6, n is about 0.2, p is between about 0.6 to about 0.2, and x is greater than 0, produce significantly higher yields of the ketones than other known metal oxides.

20 Claims, No Drawings

METHOD FOR SYNTHESIS OF KETONES FROM PLANT OILS

BACKGROUND OF THE INVENTION

1. Field of the Invention

The invention is drawn to a method for the production of ketones such as 2-undecanone or 3-dodecanone from glycerides, particularly from plant oils and most particularly glycerides of decanoic acid. The invention is also drawn to metal oxide catalysts for producing the ketones in high yields.

2. Description of the Prior Art

The coupling of organic acids to produce symmetrical ketones dates to the late 19th century when Squibb published the improved synthesis of acetone in which he demonstrated continuous production of acetone from acetic acid vapors in a red-hot iron tube [E. R. Squibb, J. Am. Chem. Soc. 17 (1895) 187-201]. Prior to this, acetone was prepared by the destructive decomposition of calcium acetate. Scheme 1 shows the formation of acetone from acetic acid along with the side products of water and carbon dioxide. The high conversions and selectivity of the reaction, along with water and carbon dioxide as lone side products, makes the process environmentally benign. Only the high temperatures required for conversion can detract from this portrayal.

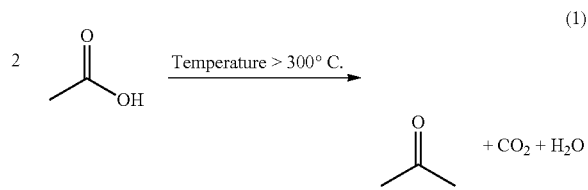

This reaction has been further developed to include the synthesis of 3-pentanone from propionic acid [O. Nagashima, S. Sato, R. Takahashi, T. Sodesawa, J. Mol. Catal. A: Chem. 227 (2005) 231-239], cyclopentanone from the cyclization of adipic acid [M. Renz, Eur. J. Org. Chem. 2005 (2005) 979-988], and larger ketones such as 7-tridecanone from heptanoic acid and its alkyl esters [C. A. Gaertner, J. C. Serrano-Ruiz, D. J. Braden, J. A. Dumesic, J. Catal. 266 (2009) 71-78; and M. Gliński, J. Kijeński, Appl. Catal., A Gen. 190 (2000) 87-91], as well as fatty acid methyl esters from rapeseed oil to give symmetrical ketones of up to 35 carbons in length [R. Klimkiewicz, H. Teterycz, H. Grabowska, I. Morawski, L. Syper, B. Licznerski, J. Am. Oil Chem. Soc. 78 (2001) 533-535]. Along with this long list of substrates, there is a list of catalysts employed in ketonizations that is even longer. At least sixteen metal oxides or carbonates including the alkaline earth metals Mg, Ca, and Ba on silica and carbon [S. Sugiyama, K. Sato, S. Yamasaki, K. Kawashiro, H. Hayashi, Catal. Lett. 14 (1992) 127-133], the rare-earth element Ce [Sugiyama et al., ibid; C. A. Gaertner, J. C. Serrano-Ruiz, D. J. Braden, J. A. Dumesic, Ind. Eng. Chem. Res. 49 (2010) 6027-6033; M. Glinski, J. Kijenski, A. Jakubowski, Appl. Catal., A Gen. 128 (1995) 209-217; and Y. Kamimura, S. Sato, R. Takahashi, T. Sodesawa, T. Akashi, Appl. Catal., A Gen. 252 (2003) 399-410], the actinides Th [S. S. Kistler, S. Swann, E. G. Appel, Ind. Eng. Chem. 26 (1934) 388-391] and U [J. Senderens, Bull. Soc. Chim. 5 (1909)], as well as the transition metals Fe [Kamimura et al., ibid], Cr [R. Swaminathan, J. C. Kuriacose, J. Catal. 16 (1970) 357-362], Mn [Gliński et al. (2000), ibid; M. Glinski, W. Szymanski, D. Lomot, Appl. Catal., A Gen. 281 (2005) 107-113; and A. D. Murkute, J. E. Jackson, D. J. Miller, J. Catal. 278 (2011) 189-199], V [R. Pestman, R. M. Koster, A. van Duijne, J. A. Z. Pieterse, V. Ponec, J. Catal. 168 (1997) 265-272], Ti [Pestman et al. ibid; and K. Parida, H. K. Mishra, J. Mol. Catal. A: Chem. 139 (1999) 73-80], Zr [Parida et al., ibid; and K. Okumura, Y. Iwasawa, J. Catal. 164 (1996) 440-448], and Ni, Co, and Cu as composite oxides [Nagashima et al., ibid].

Despite the large number of substrates and catalysts used to study the ketonization reaction, mechanistic details remain elusive and it is likely that different mechanisms occur with different catalysts. The defining characteristic which may drive the different mechanisms is the presence of an abstractable α-proton. For example, the cyclization of adipic acid in the presence of BaO or KF has been suggested to occur through a rapid deprotonation of one acid group followed in turn by decarboxylation to give a carbanion which cyclizes to form the enolate anion. This then loses the hydroxide group, which combines with the acid proton to form water, and cyclopentanone [L. Rand, W. Wagner, P. O. Warner, L. R. Kovac, J. Org. Chem. 27 (1962) 1034-1035]. This reaction also occurs, albeit at lower yields, with 2,2,5,5-tetramethyladipic acid, which lacks the α-proton. Such a mechanism is consistent with experiments based on the decomposition of acid salts but doesn't describe reactions over heterogeneous catalysts, which are becoming more common. In the ketonization of acetic acid with these catalysts, it is proposed that surface reactions occur to deprotonate or dehydrate the acid to the acetate ion and ketene, respectively. Depending on the lattice energy of the catalyst, two routes can then be followed. Low energy salts such as BaO and MgO form metal acetates which decompose to form acetone. On high lattice energy solids, the surface-bound acetate reacts with an adjacent intermediate and an adsorbed proton to give acetone. Formation of the proposed intermediate lying planar on the catalyst surface requires the abstractable α-proton [Pestman et al., ibid].

Acid esters, alcohols, and aldehydes have also been subject to ketonization studies but mechanistic information is more limited with these substrates. The reaction of n-propanol over $CeO_2$—$Fe_2O_3$ composite catalysts at 450° C. yields 3-pentanone in 61-75% but also produces hydrocarbons and CO, indicative of pyrolysis occurring at this high temperature [Kamimura et al., ibid]. The reaction of propanal over these same catalysts at 400° C. gave 3-pentanone in yields of up to 82%. Ketonization of methyl esters of fatty acids over a Sn—Ce—Rh—O catalyst gave the expected large symmetrical ketones at about 45% yield along with about 5% methylketones and 15% hydrocarbons [Klimkiewicz et al., ibid]. Here the low volatility of the substrates and products likely led to pyrolysis and low ketone yields.

SUMMARY OF THE INVENTION

We have now discovered a novel process for the production of ketones in high yields from glycerides of short chain fatty acids. The process comprises reacting the glyceride with a carboxylic acid in the presence of a catalyst and under conditions effective for ketonization of the fatty acids with the carboxylic acid to produce free ketones. In a preferred embodiment, glycerides comprising at least one ester of decanoic acid are reacted with acetic acid and/or propionic acid, producing 2-undecanone and/or 3-dodecanone, respectively. We have also discovered a novel metal oxide catalyst which produces significantly higher yields of the ketones than other known metal oxide catalysts. The novel catalysts are of the formula $Fe_mCe_nAl_pO_x$ wherein m is between about 0.2 to about 0.6, n is about 0.2, p is between about 0.6 to about 0.2, and x is greater than 0.

In accordance with this discovery, it is an object of this invention to provide a method for making ketones from glycerides such as plant oils.

Another object of this invention is to provide a method for making 2-undecanone and/or 3-dodecanone from glycerides such as plant oils.

A further object of this invention is to provide a method for producing ketones from glycerides in high yields.

Yet another object of this invention is to provide a novel catalyst for producing ketones from glycerides in high yields.

Other objects and advantages of this invention will become readily apparent from the ensuing description.

DETAILED DESCRIPTION OF THE INVENTION

The process described herein may be used to produce ketones from a variety of glycerides, including those of plant, animal or microbial origin, and particularly natural vegetable oils. Preferably the glyceride is a triglyceride, although mono- and diglycerides may be used as well. It is envisioned that the chain length of the fatty acid moieties esterified to the glycerol is not critical, and that glycerides comprising a range of esterified fatty acids may be used. Thus, glycerides suitable for use herein are generally characterized by the formula (2):

(2)

wherein $R_1$, $R_2$, and $R_3$ are independently selected from —OH or a C2 to C29 fatty acid moiety of the formula R—C(O)O— (i.e., R is a C1 to C28 straight or branched chain hydrocarbon which may be saturated or unsaturated, and may be optionally substituted) with the proviso that at least one of $R_1$, $R_2$, and $R_3$ are a fatty acid. Hence, it is possible to produce a variety of ketones having a broad range of hydrocarbon chain lengths and different levels of saturation. However, in accordance with a preferred embodiment, the glycerides comprise esters of short chain fatty acids, particularly at least one ester of decanoic acid (wherein R is an aliphatic C9 hydrocarbon), most preferably a straight chain, saturated, aliphatic C9 hydrocarbon. Reaction of these decanoate containing glycerides with acetic acid and/or propionic acid will produce free ketones comprising 2-undecanone and/or 3-dodecanone, respectively.

As starting materials for the reaction, because the glycerides, and particularly triglycerides, are the predominant component of most plant oils, naturally occurring oils may be used directly in the reaction, thereby foregoing the need for any preliminary synthesis or isolation thereof. Alternatively, animal fats, algal oils and marine oils, including fish and krill oils, may also be used. While a variety of plant oils may be used in the reaction for the production of ketones, preferred oils are those comprising a relatively high proportion of esterified decanoic acid, particularly cuphea, palm and coconut oil, with cuphea being particularly preferred. The oils comprising esterified short chain fatty acids such as decanoic acid, are relatively volatile in comparison to other oils, rendering them particularly suited for a gas phase ketonization reaction.

The ketones are produced by a catalyzed cross-ketonization reaction between the above-mentioned glyceride and carboxylic acid. Although it is envisioned that a variety of carboxylic acids may be used in the reaction, acetic acid and propionic acid are the preferred. When the carboxylic acid is represented by the general formula $R_4$—COOH, the reaction of the glyceride and carboxylic acid may be represented by the following scheme:

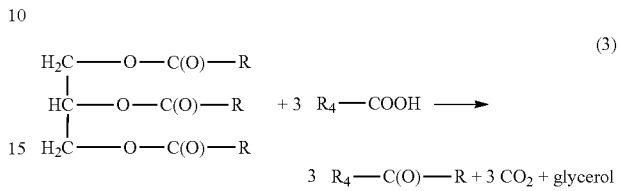

(3)

wherein R are described above, and $R_4$ is a substituted or non-substituted cyclic, straight or branched chain hydrocarbon. The carboxylic acid is preferably provided in a molar excess relative to the glyceride reactant. The large molar excess of the carboxylic acid maximizes the yield of the desired ketone product and minimizes the self-ketonization of fatty acid residues of the glyceride. Without being limited thereto, the carboxylic acid is preferably added in an amount greater than or equal to a 15-fold molar excess relative to the glyceride 15:1 carboxylic acid to glyceride), with a 23-fold molar excess being particularly preferred.

In brief, the glyceride and carboxylic acid are reacted in the presence of ketonization catalyst in an amount and under conditions effective for ketonization of the esterified fatty acid(s) of the glyceride to produce ketone. The particular catalyst used is not critical, and a variety of metal oxide or metal carbonate catalysts are suitable for use herein, including many which have been previously described for ketonization reactions and are commercially available. Thus, by way of example and without being limited thereto, suitable catalysts include the oxides or carbonates of alkaline earth metals, Mg, Ca and Ba on silica and carbon [Sugiyama et al., ibid], the rare earth element Ce [Sugiyama et al., ibid; Gaertner et al., ibid; Glinski et al. (1995), ibid; and Kamimura et al., ibid], the actinides Th [Kistler et al., ibid] and U [Senderens, ibid], transition metals Fe [Kamimura et al., ibid], Cr [Swaminathan et al., ibid], Mn [Glinski et al. (2000), ibid; Glinski et al. (2005), ibid; and Mirkute et al., ibid], V [Pestman et al., ibid], Ti [Pestman et al., ibid; and Parida et al., ibid] and Zr [Parida et al., ibid; and Okumura et al., ibid], Ni, Co, and Cu composite oxides [Nagashima et al., ibid], and Sn—Ce—Rh—Ox [Klimkiewicz et al., ibid]. However, in accordance with a preferred embodiment, we have discovered novel metal oxide catalysts of the formula $Fe_mCe_nAl_pO_x$ (wherein m is between about 0.2 to about 0.6, n is about 0.2, p is between about 0.6 to about 0.2, and x is greater than 0) which produce significantly higher yields of the ketones than other known metal oxides. The catalyst $Fe_{0.5}Ce_{0.2}Al_{0.3}O_x$ is particularly preferred. The amount of the amount of the catalyst is not critical, and may vary with the particular catalyst selected, and the reactor design, although even very small amounts are effective, and optimal amounts may be readily determined by routine experimentation.

The reaction is particularly suited for practice in fixed-bed plug-flow (FBPF) gas/solid phase flow reactor systems with the gas-phase reactants passed through and contacted in a solid catalyst bed, such as described in Example 1. FBPF gas/solid phase flow reactors are well-known in the art and a variety of such reactors are suitable for use herein. The reaction is preferably solvent-free. The reaction temperature is typically greater than approximately 350° C., preferably between 350-500° C., most preferably between 350-425° C., and the reaction is conducted substantially in the absence of oxygen (a substantially oxygen-free atmosphere). Suitable inert gas atmospheres include but are not limited to $N_2$, Ar, and He. Reaction products may be collected from the reactor, and upon cooling form a biphasic organic/aqueous fluid. The ketone product will reside in the organic aqueous layer and may be readily separated from the aqueous layer such as by decantation or evaporation. The ketone products may be separated from the glycerol by-product, for example, by distillation.

The ketonization reaction of the glycerides with carboxylic acid is advantageously conducted in a single step, without any preliminary steps for hydrolysis of the glycerides to free fatty acids.

The ketone products of the reaction, and particularly 2-undecanone, may be used as flavor and fragrance additives, and 2-undecanone has recently been described for use as an insect repellent [M. R. Roe, U.S. Pat. No. 7,288,573].

Production of the novel metal oxide catalysts of the formula $Fe_mCe_nAl_pO_x$ is described in detail in Example 1. In brief, the catalyst is prepared by coprecipitation of mixtures of Fe, Ce and Al nitrates in the selected molar ratios (i.e., m is between about 0.2 to about 0.6, n is about 0.2, p is between about 0.6 to about 0.2). Precipitation may be initiated by addition of concentrated ammonium hydroxide. The precipitated solid may be collected and dried, and then calcined by exposure to flowing air under high temperatures. The calcined solid may be optionally ground, pelletized or milled to the desired particle size. The resultant catalyst exhibits a high surface area and produces significantly greater yields of ketones, particularly 2-undecanone, than other known metal oxide catalysts. Using these catalysts, yields up to and greater than 90% (based on fatty acid residues in the glyceride) have been achieved.

The following example is intended only to further illustrate the invention and is not intended to limit the scope of the invention which is defined by the claims.

Example 1

The cross ketonization reaction with the triacylglycerol from *Cuphea* sp. and acetic acid is demonstrated. The seed oil from *Cuphea* sp. contains up to 71% decanoic acid and the reaction of this with acetic acid yields the fragrance compound 2-undecanone. Several ketonization catalysts from the literature including $CeO_2$, $CeO/Al_2O_3$, $CeO/ZrO_2$, $MnO_x/Al_2O_3$ were screened and compared with a coprecipitated mixed metal oxide of empirical formula $Fe_{0.5}Ce_{0.2}Al_{0.3}Ox$ (also represented as 50Fe20Ce30AlOx). Each of these catalysts effected the conversion but the highest yield was found with $Fe_{0.5}Ce_{0.2}Al_{0.3}Ox$. In a flow reactor, $Fe_{0.5}Ce_{0.2}Al_{0.3}Ox$ gave 2-undecanone at 91% theoretical yield with reaction conditions of 400° C., weight hourly space velocity of 2, molar ratio of acetic acid to *Cuphea* oil of 23, and $N_2$ carrier gas flow of 125 ml/min at 2.4 bar. In the absence of acetic acid, coupling of the decanoic acid residues gives 10-ketononadecane.

Experimental

Materials

*Cuphea* oil was collected and refined as described elsewhere [R. Evangelista, S. Cermak, J. Am. Oil Chem. Soc. 84 (2007) 1169-1175]. The nitrate salts were from Sigma-Aldrich (Milwaukee, Wis., USA). Neutral alumina was from Fisher Scientific (Pittsburgh, Pa., USA). Gases were from ILMO gas (Jacksonville, Ill., USA).

Catalyst Preparation

The mixed metal oxide catalyst was prepared by coprecipitation of the appropriate ratios of the nitrate salts with precipitation initiated by addition of concentrated ammonium hydroxide. Typically, 26.6 g $Fe(NO_3)_3$, 14.7 g $Al(NO_3)_3$, and 11.3 g $Ce(NO_3)_3$ were dissolved in 400 ml nanopure water. This orange solution was stirred using an overhead stirrer with a broad paddle at 250 rpm. The pH of this solution was 1.72. The addition of 55 ml of 28% ammonium hydroxide in a steady stream caused precipitation of a brown solid. The final pH was 9.40. This stirred for 5 min and was then aged, static, at room temperature overnight. The solid was collected by filtration and washed with Nanopure water. The heavy, sticky mass was allowed to air dry overnight prior to being dried in vacuo at 100° C. During this drying period, larger chunks of the solid were broken up, first with a spatula, then with a pestle. The solid was then calcined under flowing air from 25° C. to 500° C. in 5 h then held at this temperature for 30 min. Yield 11.8 g $Fe_{0.5}Ce_{0.2}Al_{0.3}Ox$. EDAX analysis: Fe, 50.3 mol %, Ce, 19.6 mol %, Al, 30.0 mol %. This was crushed with a mortar and pestle to give granules which were sieved to less than 0.5 mm. $ZrO_2$ was prepared by precipitation of $ZrO(NO_3)_3$ following a literature method [M. Rezaei, S. M. Alavi, S. Sahebdelfar, Z.-F. Yan, Powder Technol. 168 (2006) 59-63]. Ce(9)$ZrO_2$, where Ce was 9 wt % of the product, was prepared by wet impregnation by addition of a 2.45 M aqueous solution of $Ce(NO_3)_3$ onto $ZrO_2$. This was allowed to air dry and was then calcined under air at a heating ramp of 3.2° $min^{-1}$ to 600° C. to give a bright yellow powder. Ce(17)$Al_2O_3$ and Mn(20)$Al_2O_3$ were prepared likewise using commercial alumina and $Ce(NO_3)_3$ and $Mn(NO_3)_3$, respectively. These catalysts were 17 wt % and 20 wt % added metals. $CeO_2$ was prepared by the method of Jacobs et al. using urea to give a high surface area solid [G. Jacobs, S. Ricote, P. M. Patterson, U. M. Graham, A. Dozier, S. Khalid, E. Rhodus, B. H. Davis, Appl. Catal., A Gen. 292 (2005) 229-243].

Catalyst Characterization

Surface textures were determined using a Quantachrome ASiQ (Quantachrome Instruments, Boynton Beach, Fla., USA). Samples were outgassed at 200° C. for 10 h prior to analysis. Analyses were performed at −196° C. using $N_2$ as the adsorptive. Surface areas were determined using the BET equation within 0.05<P/P°<0.30. Pore sizes were determined using the BJH method on the adsorption branch of the isotherms. Temperature programmed reductions were recorded using a thermal conductivity detector and a reduction gas of 10% $H_2$ in Ar set at a flow rate of 40 ml/min. The analysis regimen was as follows. Approximately 45 mg samples were outgassed at 150° C. for 30 min, the sample cell was purged with the $H_2$/Ar mixture for 15 min and the analysis run from 150° C. to 900° C. at a heating rate of 10° C./min. Water produced by the reduction was trapped in a dry ice/ethanol bath upstream of the TCD. $H_2$ consumption was quantified by comparison to the reduction of $Ag_2O$. Temperature programmed oxidations were performed in 5% $O_2$ in Ar maintained at a flow rate of 10 ml/min. The samples were dried prior to analysis in a regimen of evacuation at 120° C. for 10 min followed by a purge with the analysis gas for 15 min. The analyses were performed with a heating ramp of 10° C./min from 120° C. to 600° C. Gases were analyzed using a Pfeiffer Prismaplus mass spectrometer.

X-ray diffraction data were collected on a Philips PW 1830 generator table with a PW1820 goniometer attached using CuKc radiation (A=0.154 nm) operating at 40 kV and 30 mA.

Product Analyses
Gas chromatography/FID

Gas chromatographic separation of the reaction mixture was accomplished on a Hewlett-Packard 6890 using a Supelco Petrocol DH 50.2 column (50 m×0.2 mm, 0.5 μm film thickness) running a heating profile of 100° C. for 2 min then ramping at 20° min$^{-1}$ to 300° C. and then at 2° min$^{-1}$ to 320° and holding for 5 min. Both the inlet and the FID were operating at 300° C.

Gas Chromatography/Mass Spectrometry (GC/MS)

An Agilent Technologies 7890A GC with a 30 m×0.25 mm i.d. HP-5MS and an Agilent Technologies 5975C mass selective detector was used for GC-MS analysis. GC conditions: helium head pressure 1 mL/min 11 psi at 100° C. set for constant flow with varying pressure; split ratio 10:1; injector temperature set at 250° C.; transfer line temperature set at 250° C.; 100° C. hold for 2 min, programmed ramp from 100 to 320° C. at 20° C./min, and hold 320° C. for 6 min. MS conditions: mass range 50-550 amu; electron multiplier 200 V relative.

Nuclear Magnetic Resonance (NMR)

$^1$H and $^{13}$C NMR spectra were collected on a Bruker Avance 500 (Billerica, Mass.) spectrometer with a 5 mm BBI probe. All spectra were acquired at 300.0 K using CDCl$_3$ as a solvent in all experiments. Chemical shifts are reported as parts per million from tetramethylsilane with an absolute frequency CH at 500.11 MHz, $^{13}$C at 125.77 MHz). Chemical shifts for $^1$H NMR spectra are reported in ppm relative to Me$_4$Si (δ 0.00) and chemical shifts for $^{13}$C NMR spectra are reported in ppm relative to the center line of the triplet corresponding to CDCl$_3$ (δ 77.00).

CHN Analyses of Coked Catalysts

CHN analyses were performed on a Perkin Elmer 2400 Series II Dumas-type elemental analyzer. Approximately 2-4 mg of material was used for each measurement. Calibration was performed using an acetanilide standard. Analyses were performed in triplicate.

Catalytic Reaction

The reactions were performed in a Parr Instruments flow reactor (Parr Instruments, Moline, Ill., USA) operating in a downward flow mode. The reactor tube was 50 cm long and 12 mm in diameter. Catalyst was loaded in the center zone such that the controlling/recording thermocouple rested at the top of the catalyst bed. The zone below the bed was filled with glass wool and glass beads and maintained at 150° C. The top zone was empty and heated to 350° C. but exceeded this due to the higher temperature at the catalyst bed. Typically, this zone was 375° C. Cuphea oil was delivered to the catalyst bed by a syringe pump (Teledyne Isco, Lincoln, Nebr., USA) while the acetic acid was delivered by an HPLC pump supplied with the reactor. The oil and acetic acid were delivered at a total weight hourly space velocity (WHSV) of two. Nitrogen flow through the reactor was 125 ml min$^{-1}$ at 2.4 bar. The substrates entered the gas stream at a T junction outside of the heated zone and were swept into the reactor. The reactor effluent was cooled in a condenser operating at 50° C. and collected in a receiver vented of gaseous products which were carried to a Pfeiffer Prismaplus mass spectrometer. Products were collected from the receiver through the drain tube as a biphasic liquid and were collected without interrupting gas flow. The organic upper layer was separated from the water layer and used for analyses. 2-undecanone: $^1$H NMR: δ 2.40 (t, J=7.6 Hz, 2H, —C(O)CH$_2$—CH$_2$—), 2.11 (s, 3H, CH$_3$—C(O)—), 1.57-1.52 (m, 2H, —C(O)—CH$_2$—CH$_2$—), 1.29-1.23 (m, 12H, —CH$_2$—), and 0.86 ppm (t, J=7.1 Hz, 6H, —CH$_2$—CH$_3$). $^{13}$C NMR: δ 209.3 (s), 43.8 (t), 31.8 (t), 29.8 (q), 29.4 (t), 29.4 (t), 29.3 (t), 29.2 (t), 23.8 (t), 22.65 (t), and 14.0 (q) ppm. MS: m/z 170 (M+, 11%), 155 (5%), 127 (5%), 71.1 (40%), and 58 (100%). 10-Nonadecanone: $^1$H NMR: δ 2.39 (t, J=7.4 Hz, 4H, —C(O)CH$_2$—CH$_2$—), 1.60-1.54 (m, 4H, —C(O)—CH$_2$—CH$_2$—), 1.32-1.26 (m, 24H, —CH$_2$—), and 0.89 ppm (t, J=7.1 Hz, 6H, —CH$_2$—CH$_3$). $^{13}$C NMR: δ 211.8 (s), 42.8 (t), 31.9 (t), 29.4 (t), 29.4 (t), 29.3 (t), 29.3 (t), 23.9 (t), 22.65 (t), and 14.1 (q) ppm. MS: m/z 282 (M+, 3%), 171 (24%), 155 (100%), 71 (60%), and 58 (33%).

Results
Catalyst Characterization

The textural properties of the catalysts and catalyst supports are shown in Table 1 and are typical of those published elsewhere. One exception is the ZrO$_2$ which has a surface area of only about a quarter of that reported for this synthetic method (74 verses 281 m$^2$/g) [Rezaei et al., ibid]. These catalysts all have literature precedent as ketonization catalysts. Al$_2$O$_3$ has been used in the reaction of acetic acid [Pestman et al., ibid], Mn(20)Al$_2$O$_3$ and Ce(17)Al$_2$O$_3$ have been shown to catalyze the reaction of alkyl heptanoates [Glinski et al. (2005), ibid], CeO$_2$ and Ce(9)ZrO$_2$ have been used on propanoic acid [Nagashima et al., ibid]. Only Fe$_{0.5}$Ce$_{0.2}$Al$_{0.3}$Ox is new and was inspired by the CeO$_2$—Fe$_2$O$_3$ catalysts of Kamimura et. al [ibid]. However, we prepared our mixed oxides by coprecipitation of nitrate salts rather than from mixtures of the molten salts, and added Al to increase surface area without adding much redox contribution to the catalyst. Indeed, Fe$_{0.5}$Ce$_{0.2}$Al$_{0.3}$Ox has a surface area more like Al$_2$O$_3$ than Fe$_2$O$_3$ (~30 m$^2$/g) or CeO$_2$ (~60 m$^2$/g). The H2 type hysteresis loop becomes more pronounced with calcination up to 500° C. and then begins to collapse at 600° C. This type of hysteresis loop is indicative of disordered pores. The results from these isotherms are presented in Table 2.

Catalytic Reaction

The fatty acid profile and the free fatty acid content of the Cuphea oil used in this study are shown in Table 3.

The cross ketonization of Cuphea oil with acetic acid yields 2-undecanone from the reaction of acetic acid with the decanoic acid residue of the oil. This is shown in Scheme 4 below. The equation is balanced with three moles of CO$_2$ and a mole of glycerol. However, since the reaction was run with a large excess of acetic acid, excess CO$_2$ and water is produced from the self ketonization of acetic acid. Glycerol was not detected in any analyses and is likely lost as coke, as is discussed below.

(4)

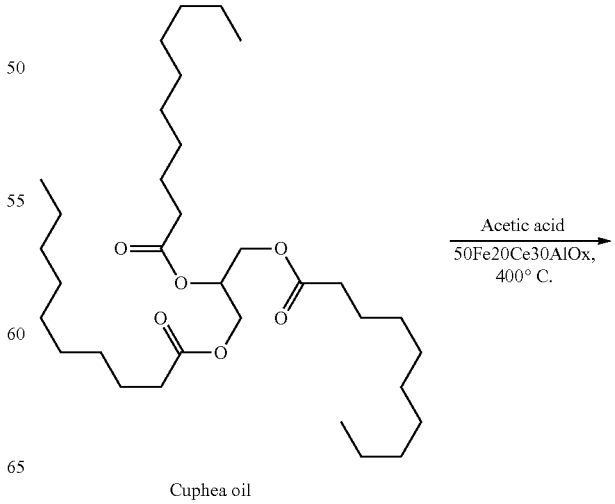

Cuphea oil → (Acetic acid, 50Fe20Ce30AlOx, 400° C.)

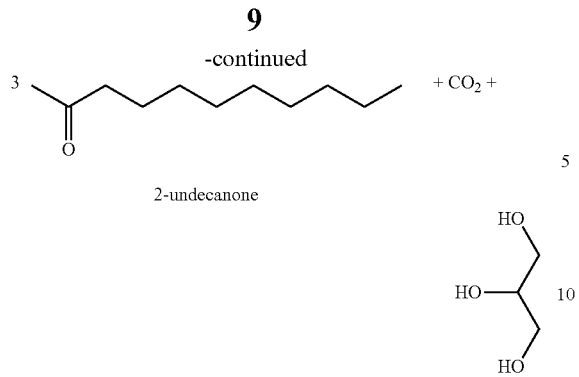

2-undecanone

Secondary products from the reaction include the analogous methylketones from the other fatty acids of the triacylglycerol, larger ketones such as 10-ketononadecane from the self ketonization of decanoic acid and analogous ketones from the other fatty acids, and acetone from the self ketonization reaction of acetic acid. Table 4 shows the yields of the primary products over the catalysts examined in this study. Owing to the high temperature of the condenser (50° C.) needed to collect the 2-undecanone as a liquid (MP 12° C.), acetone was not collected quantitatively and its yield is not reported in the table but it was detected in the GC separations of the products.

In the absence of acetic acid, 10-ketononadecane is the primary product. In the presence of 23-fold excess acetic acid the self ketonization of the fatty acid residues is minimized and the yield of 2-undecanone can be very high, reaching 91% based on decanoic acid, over $Fe_{0.5}Ce_{0.2}Al_{0.3}Ox$. Two alternative pathways are available to the decanoic acid residues that lower the yield of 2-undecanone. The catalyst supports $Al_2O_3$ and $ZrO_2$ produced 35% and 23% free decanoic acid, respectively. The production of free acid must be the result of a transesterification between the *Cuphea* oil and acetic acid rather than a simple hydrolysis since the only water present in the reactor is that from the ketonization of acetic acid and this should be carried quickly downstream of the catalyst bed. Small amounts of the transesterification coproduct, triacetin, were seen in these reactions but it was not quantified.

The second pathway for decanoic acid that would reduce 2-undecanone yields is deposition onto the catalysts resulting in coke formation. Table 5 shows the level of coke accumulation on each of the catalysts and may indicate why yields vary with each and why the $Fe_{0.5}Ce_{0.2}Al_{0.3}Ox$ catalyst performed so well. Not only does the rate of coking differ with the catalysts, H/C ratio of the resulting coke does as well. This ratio is taken as a measure of the level of saturation in the coke residue and values less than one indicate the coke is polyaromatic. The cokes deposited on alumina, ceria, zirconia, and especially $Mn(20)Al_2O_3$ have H/C ratios approaching that of saturated carbon. Only $Fe_{0.5}Ce_{0.2}Al_{0.3}Ox$ has H/C of less than one. Cokes from catalysts in petroleum refinery operations typically have H/C ratios much less than one. The H/C ratio of 0.94 is still relatively high considering the ratio for benzene is one and pyrene is 0.59. Cokes can be examined further by temperature programmed oxidation. In previous TPO studies of coked catalysts, it was shown that the composition of coke, that is its level of saturation, can be determined by the TPO profile [C. Li, T. C. Brown, Energy Fuels. 13 (1999) 888-894]. In a TPO, hydrogen on saturated carbon oxidizes at lower temperatures and this is detected as water formation in the TPO profile. The TPO profile for $Mn(20)Al_2O_3$ shows evolution of water starting at 150° C., well ahead of the evolution of $CO_2$ and CO. The profile from $Fe_{0.5}Ce_{0.2}Al_{0.3}Ox$, however, shows the evolution of all the three oxidation products starting at 225° C. and maximal $O_2$ consumption occurring at 265° C. The maximal $O_2$ consumption by $Mn(20)Al_2O_3$ occurred at 445° C. These data suggest that the coke on the $Mn(20)Al_2O_3$ originates with the saturated carbon of the *Cuphea* oil whereas the coke on the 50Fe20Ce30AlOx forms as a result of cracking of these aliphatic chains or of the glycerol backbone. Our flow reaction conditions deliver about 466 mg/h of glycerol from the *Cuphea* oil, which upon deoxygenation during coke formation would yield approximately 24 mg/h of CH residue.

TABLE 1

Textural Properties of Catalysts used for the cross ketonization

| Catalyst | BET SA, m²/g | BJH MPD, nm | BJH pore volume, cc/g | mmol H₂ consumed per g during TPH |
|---|---|---|---|---|
| $Al_2O_3$ | 175 | 3.4 | 0.214 | — |
| $CeO_2$ | 56 | 2.5 | 0.258 | 1.90 |
| $ZrO_2$ | 74 | 3.4 | 0.063 | — |
| Ce(17)Al₂O₃ | 205 | 5.6 | 0.357 | 1.37 |
| Ce(9)ZrO₂ | 67 | 3.4 | 0.078 | 0.60 |
| Mn(20)Al₂O₃ | 117 | 4.3 | 0.178 | 3.64 |
| 50Fe20Ce30AlOx | 180 | 5.6 | 0.246 | 9.40 |

TABLE 2

Surface properties of 50Fe20Ce30AlOx after calcination at 300° C.-600° C.

| Calcination Temperature, ° C. | BET surface area[1] | MPD, nm | Pore Volume, ml/g |
|---|---|---|---|
| Not calcined | 259 | 2.7 | 0.188 |
| 300 | 222 | 3.8 | 0.223 |
| 400 | 192 | 4.9 | 0.226 |
| 500 | 180 | 5.6 | 0.246 |
| 600 | 154 | 4.3 | 0.155 |

[1]m²/gram

TABLE 3

Fatty acid composition of *Cuphea* oil used in this study and level of free fatty acids in the reduced, bleached, and deodorized sample used throughout.

| Fatty acid | % Fatty acid |
|---|---|
| Caprylic acid (C8:0) | 0.49 |
| Decanoic acid (C10:0) | 70.91 |
| Lauric acid (C12:0) | 2.86 |
| Myristic acid (C14:0) | 3.96 |
| Palmitic acid (C16:0) | 5.57 |
| Stearic acid (C18:0) | 0.79 |
| Oleic acid (C18:1) | 9.87 |
| Linoleic acid (C18:2) | 5.26 |
| Linolenic acid (C18:3) | 0.29 |
| Free fatty acids | 0.62 |

TABLE 4

Yields of products from the cross ketonization of *Cuphea* oil with acetic acid over the catalysts in this study.

| Catalyst | Acetic acid: *Cuphea*[1] | Time[2] | % Yield[3] 2-Undecanone | Decanoic acid | 10-Keto-nonadecane |
|---|---|---|---|---|---|
| $Al_2O_3$ | 23 | 301 | 33 | 35 | 1 |
| $CeO_2$ | 23 | 360 | 73 | 1 | 2 |
| $ZrO_2$ | 23 | 350 | 44 | 23 | 1 |
| $Ce(17)Al_2O_3$ | 23 | 1426 | 55 | 9 | 2 |
| $Ce(9)ZrO_2$ | 23 | 359 | 78 | 1 | 3 |
| $Mn(20)Al_2O_3$ | 23 | 400 | 68 | 0 | 2 |
| 50Fe20Ce30AlOx | 23 | 1260 | 91 | 0 | 3 |

[1]Molar ratio.
[2]Time on stream in minutes.
[3]based on decanoic acid residue in the oil and taken from the last cut collected from the total time on stream. All reactions were performed at 400° C.

TABLE 5

Coke accumulation on the catalysts during ketonization of *Cuphea* oil at 400° C.

| Catalyst | Time on stream[a] | Wt % Coke[b] | H/C ratio | mg coke per hour |
|---|---|---|---|---|
| $Al_2O_3$ | 225 | 17.1 | 1.33 | 228 |
| $CeO_2$ | 360 | 9.5 | 1.14 | 78 |
| $ZrO_2$ | 350 | 15.7 | 1.31 | 132 |
| $Ce(17)Al_2O_3$ | 265 | 8.9 | — | 102 |
| $Ce(9)ZrO_2$ | 359 | 14.1 | — | 240 |
| $Mn(20)Al_2O_3$ | 301 | 21.1 | 1.54 | 210 |
| 50Fe20Ce30AlOx | 1320 | 17.1 | 0.94 | 42 |

[a]Minutes
[b]Determined by mass loss from a temperature programmed oxidation.

CONCLUSIONS

The cross ketonization of acetic acid and oil from *Cuphea* spp. can be used to prepare a sustainable supply of the fragrance compound 2-undecanone. The mixed oxide catalyst $Fe_{0.5}Ce_{0.2}Al_{0.3}Ox$ was the most efficient catalyst examined yielding 2-undecanone in 91% yield based on the decanoic acid residue in the oil. The high yield is attributed to the low level of coke formation on the catalyst.

It is understood that the foregoing detailed description is given merely by way of illustration and that modifications and variations may be made therein without departing from the spirit and scope of the invention.

We claim:

1. A method for production of ketones from glycerides comprising reacting a glyceride comprising at least one ester of decanoic acid with a carboxylic acid selected from the group consisting of acetic acid and propionic acid in the presence of a catalyst and under conditions effective for ketonization of decanoate with said carboxylic acid to produce a ketone comprising 2-undecanone or 3-dodecanone.

2. The method of claim 1 wherein said glyceride comprises a monoglyceride, diglyceride, triglyceride or combinations thereof.

3. The method of claim 2 wherein said glyceride comprises a triglyceride.

4. The method of claim 1 wherein said glyceride comprises a plant oil.

5. The method of claim 4 wherein said plant oil is selected from the group consisting of *cuphea* oil, palm oil and coconut oil.

6. The method of claim 1 wherein said carboxylic acid is present in a molar excess relative to said glyceride.

7. The method of claim 6 wherein said molar ratio of said carboxylic acid relative to said glyceride is greater than or equal to 15:1.

8. The method of claim 1 wherein said catalyst comprises a metal oxide or metal carbonate.

9. The method of claim 1 wherein said catalyst comprises $Fe_mCe_nAl_pO_x$ wherein m is between about 0.2 to about 0.6, n is about 0.2, p is between about 0.6 to about 0.2, and x is greater than 0.

10. The method of claim 9 wherein said catalyst comprises $Fe_{0.5}Ce_{0.2}Al_{0.3}Ox$.

11. The method of claim 1 further comprising recovering said ketone.

12. The method of claim 11 wherein said reacting further produces glycerol and $CO_2$ and said recovery comprises separating said ketone from said glycerol.

13. The method of claim 12 wherein said separating comprises distillation.

14. The method of claim 1 wherein said conditions comprise a temperature greater than approximately 350° C. and substantially in the absence of oxygen.

15. The method of claim 1 wherein said carboxylic acid comprises acetic acid and said ketone comprises 2-undecanone.

16. The method of claim 1 wherein said carboxylic acid comprises propionic acid and said ketone comprises 3-dodecanone.

17. The method of claim 1 wherein said reacting said glyceride with said carboxylic acid to produce said ketone is conducted in a single step.

18. The method of claim 17 wherein said reacting does not comprise hydrolyzing the glyceride to free decanoic acid.

19. A metal oxide comprising $Fe_mCe_nAl_pO_x$ wherein m is between about 0.2 to about 0.6, n is about 0.2, p is between about 0.6 to about 0.2, and x is greater than 0.

20. The metal oxide of claim 19 comprising $Fe_{0.5}Ce_{0.2}Al_{0.3}Ox$.

* * * * *